(12) United States Patent
Normand et al.

(10) Patent No.: US 10,076,549 B2
(45) Date of Patent: Sep. 18, 2018

(54) GASTRIC HEALTH SUPPLEMENT AND METHODS THEREOF

(71) Applicant: SmartPak Equine LLC, Plymouth, MA (US)

(72) Inventors: Jessica Normand, Halifax, MA (US); Kerri Vuolo, Braintree, MA (US); Lydia Gray, Elburn, IL (US); Paal C. Gisholt, Duxbury, MA (US); Michael Uckele, Blissfield, MI (US); Jack Grogan, Blissfield, MI (US); Kevin Isley, Adrian, MI (US)

(73) Assignee: SmartPak Equine LLC, Plymouth, MA (US)

( * ) Notice: Subject to any disclaimer, the term of this patent is extended or adjusted under 35 U.S.C. 154(b) by 0 days.

(21) Appl. No.: 13/688,065

(22) Filed: Nov. 28, 2012

(65) Prior Publication Data

US 2014/0147522 A1    May 29, 2014

(51) Int. Cl.
```
A61K 36/00      (2006.01)
A61K 36/185     (2006.01)
A61K 31/198     (2006.01)
A61K 36/886     (2006.01)
A23K 10/18      (2016.01)
A23K 20/147     (2016.01)
A23K 20/163     (2016.01)
A23K 20/24      (2016.01)
A23K 50/20      (2016.01)
```
(52) U.S. Cl.
CPC ............ *A61K 36/185* (2013.01); *A23K 10/18* (2016.05); *A23K 20/147* (2016.05); *A23K 20/163* (2016.05); *A23K 20/24* (2016.05); *A23K 50/20* (2016.05); *A61K 31/198* (2013.01); *A61K 36/886* (2013.01)

(58) Field of Classification Search
CPC .................................................... A61K 36/00
USPC ........................................................ 424/725
See application file for complete search history.

(56) References Cited

U.S. PATENT DOCUMENTS

| | | | |
|---|---|---|---|
| 2,868,693 A | 1/1959 | Shive et al. | |
| 6,024,959 A | 2/2000 | Bachmann | |
| 6,476,005 B1 | 11/2002 | Petito et al. | |
| 6,645,948 B2 | 11/2003 | Petito et al. | |
| 7,824,706 B2 | 11/2010 | Bedding et al. | |
| 2005/0031718 A1 | 2/2005 | Zhu et al. | |
| 2008/0050455 A1* | 2/2008 | Smith | 424/687 |

FOREIGN PATENT DOCUMENTS

| | | | |
|---|---|---|---|
| JP | 66003476 | * | 9/1962 |
| WO | WO 96/31239 | * | 10/1996 |

OTHER PUBLICATIONS

Huff et al., Journal of Veterinary Internal Medicine, Jun. 2011, vol. 25, No. 3, pp. 670-671.*
Süleyman, et al. "Antiulcerogenic Effect of Hippophae rhamnoides L." Phytotherapy Research, vol. 15, 2001, pp. 625-627.
Petro Larmo, "The Health Effects of Sea Buckhorn Berries and Oil" Retrieved from the Internet: URL:<http://www.doria.fi/bitstream/handle/1> 0024/66646/Larmo DISS1, Jan. 2011, pp. 1-103.
European Examination Report dated Apr. 5, 2018 of counterpart European Application No. 13858538.5.
European Communication and Supplementary Search Report dated Jul. 7, 2016 in counterpart European Application No. 13858538.5.
Huff, N.K. et al., "Effect of sea buckthorn berries and pulp in a liquid emulsion on gastric ulcer scores and gastric juice pH in horses," Journal of Veterinary Internal Mediciine, Sep.-Oct. 2012, vol. 26, No. 5, pp. 1186-1191.
Blitz, J.J. et al., "Aloe vera gel in peptic ulcer therapy: preliminary report," Journal A.O.A. 1963, vol. 62.
Xing, J. et al., "Effects of sea buckthorn (*Hippophae rhamnoides* L.) seed and pulp oils on experimental models of gastric ulcer in rats," Fitoterapia, 2002, vol. 73, pp. 644-650.
International Search Report dated Mar. 27, 2014 in connection with PCT/US2013/072373.

* cited by examiner

*Primary Examiner* — Michael V Meller
(74) *Attorney, Agent, or Firm* — Mintz Levin Cohn Ferris Glovsky and Popeo, P.C.; Peter F. Corless

(57) ABSTRACT

The invention provides novel compositions that can be used as a supplement (e.g. feed supplement) to animals such as, horses. In certain embodiments, the composition comprises an effective amount of a preparation obtained from sea buckthorn and an effective amount of an amino acid. In other embodiments, the composition includes specific combinations of components selected from the group of a preparation obtained from sea buckthorn, glutamine, aloe vera extract, pectin, and lecithin. The invention also provides methods and uses of the composition for alleviating, treating or preventing an ulcer-related condition in a subject identified in need thereof.

1 Claim, 11 Drawing Sheets

| Lesion Number-Grade | Description |
|---|---|
| 0 | No lesions |
| 1 | 1-2 localized lesions |
| 2 | 3-5 localized lesions |
| 3 | 6-10 lesions |
| 4 | 10 or more lesions or diffuse (very large) lesions |

| Lesion Severity-Grade | Description |
|---|---|
| 0 | No lesions |
| 1 | Appears superficial |
| 2 | Deeper structures involved |
| 3 | Multiple lesions |
| 4 | Deeper structures involved and has active appearance (hyperemic or darkened) |
| 5 | Same as number 4 plus hemorrhage or blood clot |

FIG 2

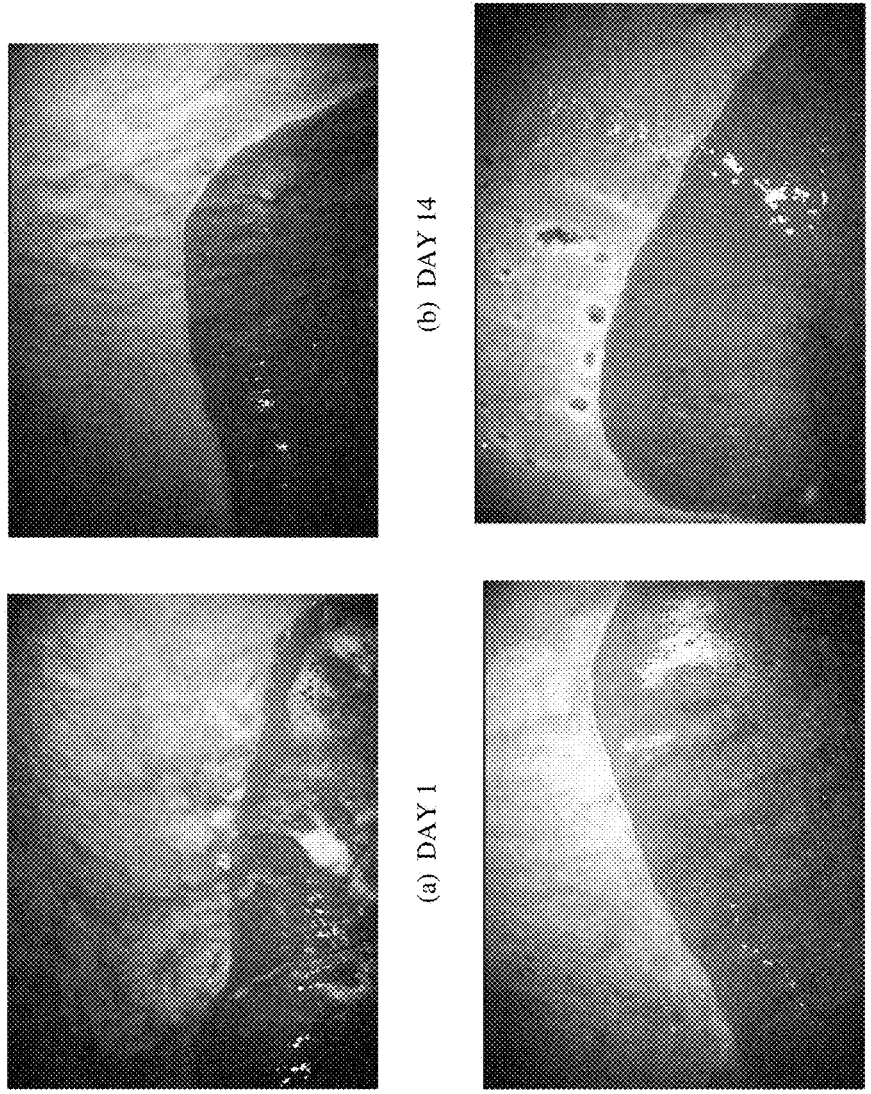
FIG 3 (a-d)

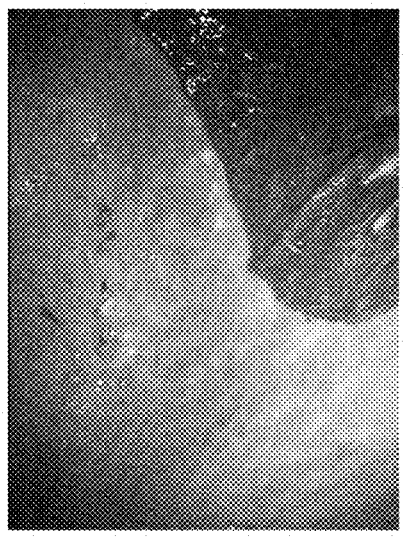
(a) DAY 1
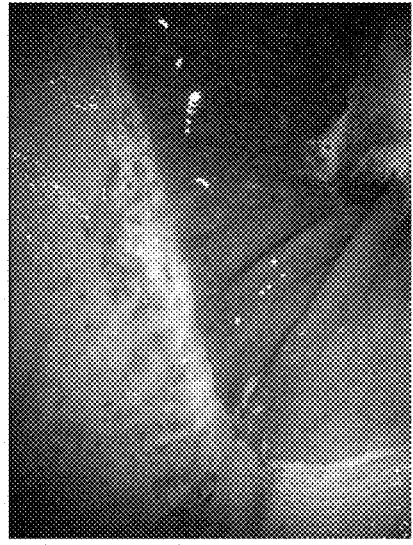
(b) DAY 14
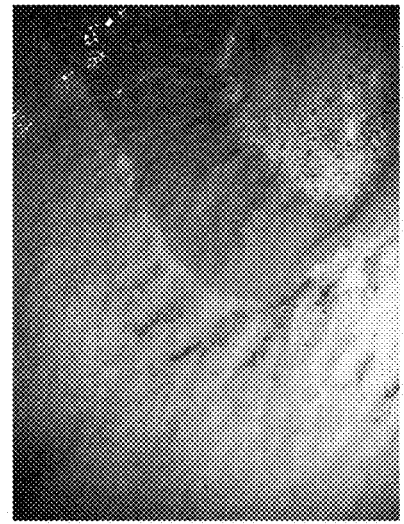
(c) DAY 28
(d) DAY 35
FIG 4(a-d)

| HORSE # | TREATMENT | SCORE | | | |
|---|---|---|---|---|---|
| | | Day 0 | Day 30 | Day 60 | Day 67 |
| 10 | Control | 2 | 0 | 0 | 2 |
| 12 | Control | 0 | 0 | 0 | 1 |
| 28 | Control | 2 | 1 | 1 | 2 |
| 11 | Control | 2 | 0 | 2 | 3 |
| 08 | Control | 1 | 3 | 1 | 3 |
| 20 | Control | 3 | 2 | 2 | 1 |
| 36 | Control | 2 | 2 | 1 | 1 |
| 09 | Control | 2 | 2 | 2 | 3 |
| Mean | | 1.8 | 1.0 | 1.1 | 2.0 |
| Range | | (0-3) | (0-3) | (0-2) | (1-3) |
| 10 | SBT | 3 | 0 | 1 | 2 |
| 12 | SBT | 0 | 0 | 0 | 0 |
| 28 | SBT | 3 | 2 | 2 | 2 |
| 11 | SBT | 1 | 2 | 0 | 0 |

FIG 8

| HORSE # | TREATMENT | pH | | | |
|---|---|---|---|---|---|
| | | Day 0 | Day 30 | Day 60 | Day 67 |
| 10 | Control | 5.05 | 2.74 | 2.59 | 4.22 |
| 12 | Control | 6.3 | 5.61 | 2.03 | 1.86 |
| 28 | Control | 1.9 | 2.07 | 1.75 | 1.35 |
| 11 | Control | 5.26 | 2.03 | 2.96 | 1.56 |
| 08 | Control | 0.84 | 1.83 | 1.66 | 1.8 |
| 20 | Control | 1.95 | 1.52 | 1.45 | 1.78 |
| 6 | Control | 0.56 | 1.8 | 1.14 | 1.45 |
| 09 | Control | 0.75 | 1.51 | 1.25 | 1.46 |
| Mean | | 2.83 | 2.39 | 1.85 | 1.94 |
| S.D. | | 2.33 | 1.36 | 0.64 | 0.94 |
| 10 | SBT | 0.71 | 3.82 | 1.42 | 1.9 |
| 12 | SBT | 1.33 | 1.46 | 1.38 | 1.93 |
| 28 | SBT | 0.35 | 1.46 | 1.46 | 1.8 |
| 11 | SBT | 1.49 | 1.88 | 4.44 | 1.93 |
| 08 | SBT | 5.81 | 6.24 | 2.69 | 1.82 |
| 20 | SBT | 2.66 | 1.75 | 4.4 | 2.29 |
| 36 | SBT | 1.71 | 2.03 | 2.02 | 1.66 |
| 09 | SBT | 3.49 | 3.25 | 2.06 | 1.64 |
| Mean | | 2.19 | 2.74 | 2.48 | 1.87 |
| S.D. | | 1.77 | 1.68 | 1.27 | 0.20 |

FIG 9

GASTRIC HEALTH SUPPLEMENT AND METHODS THEREOF

BACKGROUND

Equine Gastric Ulcer Syndrome (EGUS) is a common medical problem in horses. The prevalence of EGUS ranges from 60 to 90% among performance horses. Ulcers occur primarily in the non-glandular (squamous) portion of the stomach of a horse due to its lack of resistance to the erosive effects of gastric acids, including, hydrochloric, volatile fatty and bile acids. Horses with EGUS usually perform poorly, which makes it a significant economical problem within the horse industry.

Although several pharmaceutical treatments are currently available, these treatments are expensive. Besides, it has been found that certain therapeutic agents reduce the acidic environment of the stomach, which may affect digestion of the horses. For example, the FDA-approved pharmaceutical agent GASTROGARD® (omeprazole; Merial Ltd., Duluth, Ga.), a proton pump inhibitor, has been shown effective in treating equine ulcers. However, an omeprazole treatment is generally accompanied with an increased gastric juice pH value in horses, thus possibly negatively affecting digestion of forage and feed.

Therefore, there is a need to develop alternative methods and/or therapeutics that are effective in alleviating, treating, or preventing an ulcer-associated condition (e.g., Equine Gastric Ulcer Syndrome) in horses. Preferably, the new method and/or therapeutic would also offer a less expensive alternative and/or supplement to the current pharmaceutical treatments.

SUMMARY

One aspect of the invention provides a novel composition that can be used as a food supplement. Specifically, the composition includes an effective amount of a preparation obtained from sea buckthorn and an effective amount of an amino acid.

One embodiment provides that the preparation obtained from sea buckthorn is a concentrate, metabolite, constituent, or extract, or a combination thereof of the sea buckthorn fruits. For example, the preparation used herein is a sea buckthorn fruit powder.

The amino acid in a composition of the invention can be any amino acid that may be included in a food product. In one embodiment, the amino acid used herein is glutamine (e.g., L-glutamine).

A composition of the invention may further comprise one or more additional components, such as aloe vera extract, pectin, and lecithin.

Another aspect of the invention relates to a supplement (e.g. a health supplement), which includes a composition of the invention. Such a supplement may be, for example, used as a feed supplement to an animal (e.g., an animal of equidae family). In certain embodiments, the supplement of the invention may further contain one or more additional nutrients, such as, vitamins, minerals, amino acids, proteins, herbs, oils, or combinations thereof. In certain embodiments, the additional nutrient is a vitamin.

The invention also provides feed supplement formulations. The formulations may be included in a feed supplement to horses. In certain embodiments, the feed supplement formulation of the invention comprises a preparation obtained from sea buckthorn, and one or more additional components selected from the group of aloe vera extract, glutamine, pectin, and lecithin.

In one embodiment, the additional component is aloe vera extract. In another embodiment, the additional component is glutamine (e.g., L-glutamine). Alternatively, the additional component is pectin (e.g., citrus pectin). In still another embodiment, the additional component of the feed supplement formulation is lecithin.

In a separate aspect, the invention provides a novel horse supplement. Certain embodiments provide that the horse supplement of the invention comprises at least two different components, with a first component being lecithin or glutamine, and a second being aloe vera extract, lecithin, or glutamine (e.g., L-glutamine). In another embodiment, such a horse supplement includes an effective amount of a preparation obtained from sea buckthorn fruits.

It has been shown that the horse supplement of the invention does not significantly alter a gastric juice pH value of a horse subsequent to its administration to the horse. By stating that the pH value is not significantly altered, it is meant that the gastric juice In a further aspect, the invention provides an animal feed, which comprises a composition or formulation described herein.

The invention also relates to a feed supplement formulation. The formulation comprises an effective amount of active ingredients including glutamine and a sea buckthorn fruit powder. More specifically, in one aspect, the glutamine is suitably present at about 500 to 50,000 mg and the sea buckthorn is present at about 500 to 50,000 mg. In a further embodiment, glutamine is present at about 5 to 20 weight percentage of the active ingredients in the formulation (excluding fillers and binders like alfalfa), and the sea buckthorn, and the sea buckthorn fruit powder is present at about 5 to 20 weight percentage of the active ingredients in the formulation.

The formulation of the invention may be in a solid or liquid form. In one embodiment, it is in a pellet form.

In one example, the glutamine is L-glutamine, which is in an amount of about 1 to 20% w/w of the active ingredients in the formula, suitably about 2 to 10 or 15% w/w of the active ingredients in the formula, such as about 7.5% w/w of the active ingredients in the formula. As a separate example, the sea buckthorn fruit powder is at an amount of about 1 to 20% w/w of the active ingredients in the formula, suitably about 2 to 10 or 15% w/w of the active ingredients in the formula, such as about 6.25% w/w of the active ingredients in the formula.

In still another aspect, the invention provides a method of alleviating, treating, or preventing an ulcer-associated condition in a subject identified in need thereof. In certain embodiments, the method involves administering to the subject a composition or formulation described herein. In certain embodiments, the composition or formulation of the invention is administered together with food (e.g., a feed). The administration can be an oral administration.

In a further embodiment, the product is top-dressed on feed.

One embodiment provides that the subject is a mammal, such as, a horse. The condition being alleviated, treated, or prevented by the method of the invention is associated with an ulcer in the subject. Embodiments of the invention provide that the ulcer is a gastric ulcer, stomach ulcer (or peptic ulcer), venous ulcer, ulcerative sarcoidosis, ulcerative lichen planus, ulcerative colitis, mouth ulcer, corneal ulcer, or dermatological ulcers. Specifically, the ulcer is a gastric ulcer or stomach ulcer.

In one embodiment, the method of the invention is used for alleviating, treating, or preventing Equine Gastric Ulcer Syndrome (EGUS) in horses.

In another aspect, methods are provided to alleviate, treat, or prevent an ulcer-associated condition in a subject identified in need thereof, comprising administering to the subject an effective amount of a composition wherein gastric juice pH value of the subject is not significantly altered and the ulcer-associated condition is treated. In a preferred aspect, the subject is a horse and administration of the composition treats the ulcer-associated condition of the horse but the horse gastric juice pH does not significantly change. By stating that the pH does not "significantly change" it is meant that the pH of the test subject's gastric juice is tested one hour prior to administration of the composition and one hour after administration of the composition, and those two tested pH values do not differ by more than 2.0, more preferably not more than 1.5, still more preferably those two tested pH values do not differ by more than 1.0, 0.5 or 0.25. Gastric juice pH values as referred to herein can be determined as follows: gastric juice of a subject animal (e.g. horse) is aspirated through the biopsy channel of an endoscope and pH is measured at specified time intervals, particularly 1 hour before and then 1 hour after administration of a therapeutic agent or Supplement composition as disclosed herein. Gastric juice pH values can be compared between the times.

In such methods to alleviate, treat, or prevent an ulcer-associated condition in a subject (e.g. horse) identified in need thereof, an effective amount of a Supplemental composition as disclosed herein can be administered wherein gastric juice pH value of the subject (e.g. horse) is not significantly altered and the ulcer-associated condition is treated.

The method of the invention may further comprise a step of administering to the subject an amount of a therapeutic agent that is effective in treating or preventing an ulcer-related disease or condition. In one embodiment, the therapeutic agent is any form of omeprazole (under tradename GASTROGARD®), ULCERGARD®, PRILOSEC or such other forms of omeprazole that may be sold by compounding pharmacies or others) or a pharmaceutically effective salt, solvate, hydrate, diastereomer, produg, or metabolite thereof The therapeutic agent can be administered to the subject prior to, concurrently with, or subsequent to the administration of the composition or formulation of the invention. In a more specific embodiment, the formulation of the invention is administered after administration of the therapeutic agent to prevent rebound ulcers. More specifically, the formulation of the invention is administered after the administration of GASTROGARD® to prevent rebound ulcers in horses In accordance with the invention, the composition or formulation described herein can be administered to the subject once or multiple times a day. For example, the composition is administered once, twice or three times a day.

It is believed that the method of the invention achieves its intended purpose(s) without significantly altering a gastric juice pH value of the subject.

Other aspects of the invention include a kit which contains a composition or formulation described herein. The kit may come with written instructions for administration of the composition or formulation to a subject, such as, a wide variety of animals including, specifically, a horse.

Other aspects of the invention are discussed infra.

BRIEF DESCRIPTION OF THE DRAWINGS

FIG. 2 is a table presenting MacAllister (1997) gastric ulcer number and severity scoring system.

FIG. 3 (a-d) are gastroscopic images of the non-glandular mucosa in a horse treated with a Supplement composition of Example 1.

FIGS. 4 (a-d) are gastroscopic images of the non-glandular mucosa in a control horse.

FIG. 8 is a table showing non-glandular gastric ulcer scores for untreated control (Contro) horses (n=8) and those treated by a composition containing sea buckthorn berries (SBC; marked as SBT) after an alternating feed deprivation model.

FIG. 9 is a table showing gastric juice pH values in untreated control horses (n=8) and those treated by a composition containing sea buckthorn berries (SBC; marked as SBT) after an alternating feed deprivation model.

DETAILED DESCRIPTION

Figure 1:
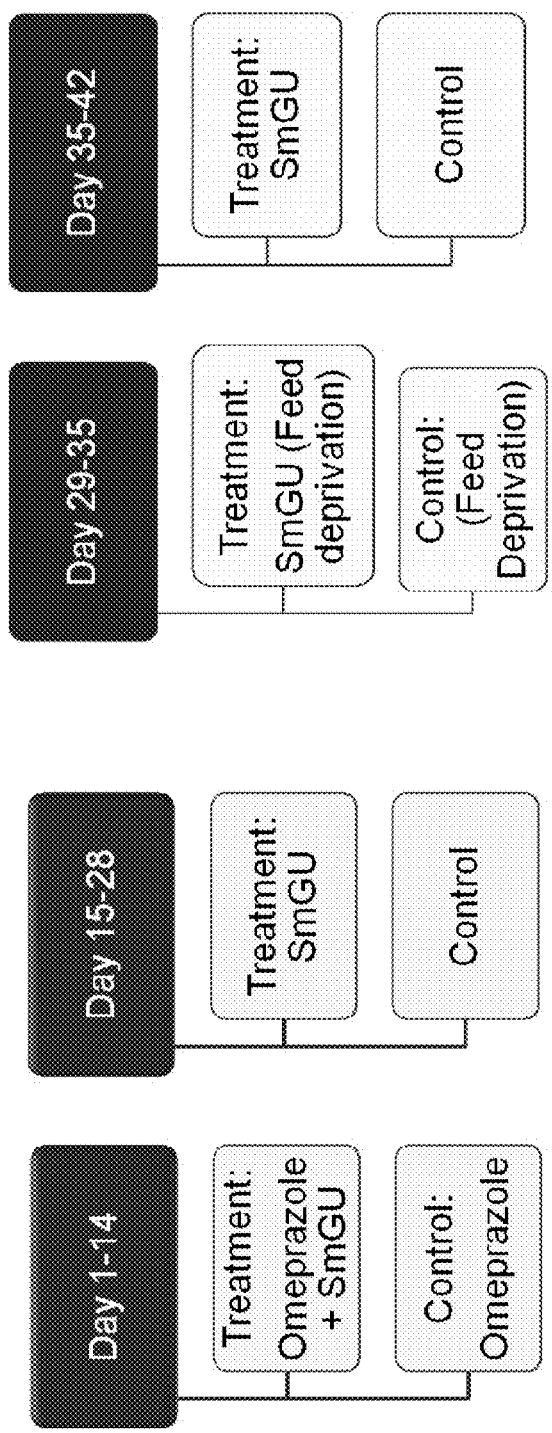
FIG. 1 is a graph showing timeline of events occurring during each period of a 42-day equine health study treating horses with a Supplement composition of Example 1 (referred to as SmGU) and/or omeprazole.

In one aspect, the invention features provides novel compositions that can be used as a supplement to animals (e.g., a horse).

In certain embodiments, a composition of the invention includes an effective amount of a preparation obtained from sea buckthorn and an effective amount of an amino acid. In other embodiments, a composition of the invention includes a preparation obtained from sea buckthorn, and one or more additional components selected from the group of aloe vera extract, glutamine, pectin, and lecithin. Alternatively, a composition of the invention may contain at least two different components, wherein a first component is lecithin or glutamine, and a second component is aloe vera extract, lecithin, or glutamine.

Berries and pulp from the sea buckthorn plant (*Hippophae rhamnoides*) are a rich source of vitamins, trace minerals, amino acids, antioxidants, and other bioactive substances. Thus, attempts have been made to use the sea buckthorn berries and pulp to treat mucosal injury including, decubital ulcers, burns, and stomach and duodenal ulcers in man and rats (Geetha et al. 2002; Beveridge et al. 1999; Xing et al. 2002).

With a purpose of treating or preventing Equine Gastric Ulcer Syndrome (EGUS) in horses, another inventor introduced a commercially available product containing sea buckthorn berries (SBC: SEABUCK™ Complete) as a feed additive for horses. Although the SBC treatment failed to significantly decrease gastric ulcer scores in the horses being treated, it was suspected that active ingredients contained in sea buckthorn berries may have some efficacy in preventing worsening of the ulcer conditions in the treated horses (see FIGS. 8-11) when combined in certain amounts with another component or components.

The invention is based, in part, on the discovery of specific compositions containing certain combinations of active ingredients (such as, a preparation obtained from sea buckthorn and an amino acid) can successfully prevent the worsening of naturally occurring gastric ulcers after an omeprazole treatment in horses having EGUS. It is believed that certain compositions of the invention achieve this object without significantly altering gastric juice pH values in the horses.

The invention also provides a method of alleviating, treating, or preventing an ulcer-associated condition in a subject identified in need thereof. The subject described herein is a mammal, such as, a horse. In addition, the invention provides methods as a facile means to identify treatments that are safe/effective for treating an ulcer-associated condition in the subjects.

DEFINITIONS

Before a further description of the present invention, and in order that the invention may be more readily understood, certain terms are first defined and collected here for convenience.

The term "administration" or "administering" includes routes of introducing a composition, formulation, or product to a subject to perform its intended function. Examples of routes of administration that can be used include oral, injection (subcutaneous, intravenous, parenterally, intraperitoneally, intrathecal), inhalation, rectal and transdermal. The preparations (e.g., composition, formulations, or products) are, of course, given by forms suitable for each administration route. For example, the preparations may be administered in tablets or capsule form, by a powder or pellets fed separately, by powder or pellets top dressed on food or feed, by injection, inhalation, topically by lotion or ointment; and rectally by suppositories. According to certain embodiments of the invention, oral administration is preferred. The injection can be bolus or can be continuous infusion. Depending on the route of administration, the active ingredients of the preparations can be coated with or disposed in a selected material to protect them from natural conditions which may detrimentally affect their ability to perform their intended function.

The composition, formulations, or products can be administered alone, or in conjunction with other nutrients or therapeutic agents, or with a carrier acceptable for use in food/feed industries, or both. The composition, formulations, or products can be administered prior to, simultaneously with, or after the administration of the other nutrients or therapeutic agents. Furthermore, the composition, formulations, or products can also be administered in a preform which is converted into its active form (e.g., metabolite), or more active form in vivo.

The term "ameliorate" means to decrease, suppress, attenuate, diminish, arrest, or stabilize the development or progression of a disease, disorder, or condition.

The term "alleviate" means to lighten, lessen, relieve, decrease, suppress, attenuate, diminish, or make more bearable of symptoms associated with a disease, disorder, or condition.

The term "alteration" refers to a change (increase or decrease) in a parameter as detected by standard art known methods, such as those described herein.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments. "Detect" refers to identifying the presence, absence or amount of the object to be detected.

By "disease" is meant any condition or disorder that damages or interferes with the normal function of a cell, tissue, or organ.

The term "diastereomers" refers to stereoisomers with two or more centers of dissymmetry and whose molecules are not mirror images of one another.

The term "effective amount" or "pharmaceutically effective amount" refers to the amount of an agent required to ameliorate, alleviate, treat, or prevent the symptoms of a disease, disorder, or condition relative to an untreated subject. The effective amount of active ingredients used to practice the present invention may vary depending upon the manner of administration, the age, body weight, and general health of the subject. Ultimately, the attending physician or veterinarian will decide the appropriate amount and dosage regimen. Such amount is referred to as an "effective" amount.

An effective amount of a component or composition delineated herein (i.e., an effective dosage) may range from about 0.1 µg to 20 gram per kilogram of body weight per day (mg/kg/day) (e.g., 0.1 µg/kg to 2 g/kg). In other embodiments, the amount varies from about 0.1 mg/kg/day to about 100 g/kg/day. In still other embodiments, the amount varies from about 0.001 µg to about 10 g/kg (e.g., of body weight). Alternatively, the effective amount of a component or active ingredient in a composition ranges from 0.01% to 100% w/w. In certain embodiments, the amount varies from about 0.1% to 80%, or 0.5% to 50% w/w. In still other embodiments, the amount varies from about 1% to about 20% w/w, 5% to about 20% w/w, or 5% to about 10% w/w.

One of skill in the art can readily extrapolate from dosages shown to be effective in in vivo testing the dosages that are likely to be effective in the subject (e.g., a mammal). The skilled artisan will appreciate that certain factors may influence the amount required to effectively treat a subject, including but not limited to the severity of the disease, disorder, or condition, previous treatments, the general health and/or age of the subject, the body weight of the subject being treated, and other diseases or conditions present. Moreover, treatment of a subject with an effective amount of a composition delineated herein can include a single treatment or a series of treatments.

If desired, the dosage is administered one time per day, two times per day, three times per day, or four times per day. Alternatively, the dosage is administered one time every two days, one time every three days, one time every four days, one time every five days, one time every six days, or one time per week. It will also be appreciated that the effective dosage of a composition delineated herein used for its intended purpose may increase or decrease over the course of a particular treatment.

The term "extract" refers to a substance made by extracting a part of a raw material (such as, plants, fruits, blossoms, roots, seeds, vegetables, etc.). Without wishing to be bound by any theory, it is contemplated that an extraction process often involves using a solvent such as alcohols or water. Extracts may be in tinctures or in powder form.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "isotopic derivatives" includes derivatives of compounds in which one or more atoms in the compounds are replaced with corresponding isotopes of the atoms. For example, an isotopic derivative of a compound containing a carbon atom ($C^{12}$) would be one in which the carbon atom of the compound is replaced with the $C^{13}$ isotope.

The term "inflammation" as used herein refers to a way in which the body reacts to infection, irritation or other injury, the key feature being redness, warmth, swelling and pain. The inflammatory response directs one's immune system components to the site of injury or infection and is manifest by increased blood supply and vascular permeability which allows chemotactic peptides, neutrophils, and mononuclear cells to leave the intravascular compartment. Microorganisms are engulfed by phagocytic cells (e.g., neutrophils and macrophages) in an attempt to contain the infection in a small-tissue space. The response includes attraction of phagocytes in a chemotactic gradient of microbial products, movement of the phagocyte to the inflammatory site and contact with the organism, phagocytosis (ingestion) of the organism, development of an oxidative burst directed toward the organism, fusion of the phagosome and lysosome with degranulation of lysosomal contents, and death and degradation of the organism. Staphylococci, gram-negative organisms, and fungi are the usual pathogens responsible for these infections (see definitions from MediciNet.com). Macrophages secrete a number of cytokine proteins that, when bloodborne, cause a more generalized or systemic inflammation (sepsis). Sepsis may develop rapidly and is a life threatening disorder in need of new drug therapies.

The term "metabolite" as used herein refers to an intermediate or product of a biologically active compound as result of metabolism. Metabolites may have various functions, including fuel, structure, signaling, stimulatory and inhibitory effects on enzymes, catalytic activity of their own (usually as a cofactor to an enzyme), defense, and interactions with organisms.

The term "modulate" refers to increases or decreases in a parameter of the disease, disorder, or condition in response to exposure to a composition of the invention.

The term "optical isomers" as used herein includes molecules, also known as chiral molecules, are exact non-superimposable mirror images of one another.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The terms "livestock" refers to domesticated, semi-domesticated, or captive wild animals. In certain embodiments, livestock refers to domesticated animals that are raised in an agricultural setting. In other embodiments, livestock also includes pets such as, dogs and cats. For example, livestock may include alpaca, banteng, bison, camel, cat, cattle, deer, dog, donkey, gayal, goat, guinea pig, horse, llama, mule, pig, rabbit, reindeer, sheep, buffalo, yak, and etc.

The term "polymorph" as used herein, refers to solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing.

The term "prodrug" includes inactive compounds with moieties that can be metabolized in vivo. (or which spontaneously are transformed within the body as a result of their chemical instability) into an active drug. Generally, prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Certain prodrug moieties are, for example, propionoic acid esters and acyl esters. Prodrugs which are converted to active forms through other mechanisms in vivo are also included.

With respect to the nomenclature of a chiral center, the terms "D" and "L" configuration are as defined by the IUPAC Recommendations. Of the standard α-amino acids, all but glycine exist in either of two enantiomers, called "L" or "D" amino acids, which are mirror images of each other. In certain instances, the terms "R" and "S" may be used to define the configuration of a compound. As to the use of the terms, diastereomer, tautomer, racemate, and enantiomer, these will be used in their normal context to describe the stereochemistry or regiochemistry of preparations.

By "reference" is meant a standard or control condition.

The term "subject" includes organisms which are capable of suffering from a disease, disorder or condition described herein or who could otherwise benefit from the administration of a composition of the invention, such as, a mammal (e.g., livestock) or other types of animals.

The phrases "systemic administration," "administered systemically", "peripheral administration" and "administered peripherally" as used herein mean the administration of a composition, drug or other material, such that it enters the subject's system and, thus, is subject to metabolism and other like processes, for example, subcutaneous administration.

Compositions, Formulations and Other Products

The invention provides novel compositions that can be used as a supplement (e.g., a health supplement). Specifically, a composition of the invention includes a mixture of botanicals and other ingredients, as active ingredients effective in protecting a stomach of a mammal from erosive effects of gastric acids. Examples of suitable botanicals may be taken from a wide variety of sources, such as, fruits, vegetables, flowers, seeds, roots, and plants. In certain embodiments, the botanical included in the composition is a preparation obtained from sea buckthorn. One example provides that the preparation is a concentrate, metabolite, constituent, or extract, or a combination thereof of sea buckthorn fruits.

Thus, in certain embodiments, a composition of the invention comprises an effective amount of a preparation obtained from the sea buckthorn and an effective amount of an amino acid.

One embodiment provides that the preparation obtained from sea buckthorn is a concentrate, metabolite, constituent, or extract, or a combination thereof of the sea buckthorn fruits.

The preparation may contain all or most biologically active components that are found in the sea buckthorn. Alternatively, the preparation may contain derivatives of these biologically active components. The derivatives may be generated during a process of obtaining the preparation.

Such derivatives include, for example, salts, hydrates, solvates, polymorphs, metabolites, prodrugs, isotopic derivatives, clathrates, isomers, by-products, or combinations thereof of a biologically active compound. In addition, the preparation obtained from the sea buckthorn may include chemicals and/or other components, which are added during a preparing process. The added chemicals and/or other components can be synthetic or nature occurring. The chemicals and/or other components can be biologically active or inactive. The preparation obtained from the sea buckthorn may also contain impurities.

The preparation used herein can be in a liquid or solid form (such as, a powered or granulated form). In one embodiment, the preparation is a sea buckthorn fruit powder.

A composition of the invention may contain from 0.1 to about 99 percent by weight of a preparation obtained from botanicals (e.g., sea buckthorn fruits), either in a solid or liquid form. In certain embodiments, the sea buckthorn fruit powder is present at about 5 to 20 weight percentage of the composition. One example provides that the sea buckthorn fruit powder is at about 6.25% w/w.

The amino acid in the compositions of the invention can be any amino acids that are included in a food product. Amino acids, as the basic components of proteins, have long represented the most economical and efficient means for adapting the protein composition of the diets of animals bred to the increasing needs dictated by genetic improvement and the qualitative demands of the market for products of animal origin.

Amino acids may come from chemical synthesis or fermentation processes, and are available to the animal feed industry either in powder or liquid form, chemically formulated either as natural-like amino acids or as various chemical derivatives, which are then metabolized by the animal in biologically active amino acids.

Typical amino acids include alanine, beta-alanine, arginine, asparagine, aspartic acid, carnitine, citrulline, cysteine, cystine, γ-aminobutryic acid, glutamic acid, glutathione, glycine, glutamine, histidine, hydroxyproline, isoleucine, leucine, lysine, methionine, ornithine, phenylalanine, proline, serine, taurine, threonine, tryptophan, tyrosine and valine. The amino acids that may be used in a composition of the invention can be in a D- or L-configuration or both.

Further, the composition of the invention may include any commercial amino acids, for example, those provided in SMARTAMINE® and RHODIME® AT 88, available from Rhone Poulenc Animal Nutrition, Atlanta, Ga., and LysMet available from SILO S.r.l., Firenze, Italy.

In one embodiment, the amino acid included in a composition of the invention is glutamine, more specifically, L-glutamine.

A composition of the invention may further include one or more different amino acids. For example, glycine may be in combination with glutamine to be included in the composition.

The amino acid(s) may be present at about 1 to 50 weight percentage of the total weight of the composition. One embodiment provides that the amino acid(s) is at about 5 to 20 weight percentage. In one example, glutamine is at about 5% to 10% of the total weight of the composition. Another example provides that L-glutamine and glycine are at about 7.5% and about 1.25%, respectively.

A composition of the invention may further comprise one or more additional components, such as, aloe vera extract, pectin, and lecithin.

For example, the additional component of a composition of the invention is aloe vera extract. Another example provides that the additional component is glutamine (e.g., L-glutamine). In a separate embodiment, the additional component is pectin (e.g., citrus pectin). In another embodiment, the additional component is lecithin.

The aloe vera extract referred to herein is a preparation made from the plant Aloe vera. The aloe vera extract can be in any form, including, such as, gel, juice, powder, and etc. It is contemplated that the amount of the aloe vera extract included in a composition of the invention does not cause any toxic effects in a subject to whom the composition is administered.

Pectin, also known as pectic polysaccharides, is a heteropolysaccharide. Pectins that may be used in the present invention can be those contained in extracts from natural products (e.g., sugar beet, potatoes, and pears). Alternatively, pectins used herein may be synthetically prepared. In addition, the term "pectin" used herein also includes modified forms of pectin, for example, amidated pectin. In one embodiment, a composition of the invention includes citrus pectin.

Lecithin refers to a group of fatty substances that are generally composed of phosphoric acid, choline, fatty acids, glycerol, glycolipids, triglycerides, and/or phospholipids (e.g., phosphatidylcholine, phosphatidylethanolamine, and phosphatidylinositol). Lecithin may be naturally-occurring (e.g., those contained in animal and plant tissues). Lecithin can be obtained by degumming extracted oil of seeds. In addition, lecithin used in the invention can be synthetically prepared, which includes modified forms (such as, hydrolyzed lecithin). One example of lecithin used in the invention is obtained from soybeans.

Further, the invention provides a supplement, which includes a composition described herein. Such a supplement may be, for example, used as a feed supplement to an animal (e.g., a horse). In certain embodiments, the supplement of the invention may further contain one or more additional nutrients, such as, vitamins, minerals, amino acids, proteins, herbs, oils, or combinations thereof. In certain embodiments, the additional nutrient is a vitamin.

The invention also provides feed supplement formulations. The formulations may be included in a feed supplement to horses. In certain embodiments, the feed supplement formulation of the invention comprises a preparation obtained from sea buckthorn, and one or more additional components selected from the group of aloe vera extract, glutamine, pectin, and lecithin.

A novel horse supplement is also provided herein. For example, the horse supplement of the invention may comprise at least two different components, with a first component being lecithin or glutamine (e.g., L-glutamine), and a second being aloe vera extract, lecithin, or glutamine (e.g., L-glutamine). In one embodiment, the horse supplement includes an effective amount of a preparation obtained from sea buckthorn fruits.

It is believed that the horse supplement of the invention does not significantly alter a gastric juice pH value of a horse subsequent to its administration to the horse. In a further aspect, the invention provides an animal feed, which comprises a composition or formulation described herein.

The composition or formulation of the invention may include one or more additional biologically active and/or inactive components. Such components can be, such as, surfactants, disintegrants, diluents, stablizers, preservatives, buffers, fillers, plasticizers, lubricants, excipients, and etc. Additional components that can be included in a supplement are known to those of ordinary skill in the art.

Certain additional components for the compositions can be, but are not limited to, such as, calcium carbonate, magnesium carbonate, magnesium silicate, hydrolyzed or unhydrolyzed collagen, deglycyrrized licorice, fructooligosaccharides (FOS), mannanoligosaccharides (MOS), gamma oryzanol, slippery elm, marshmallow root extract, sodium copper chlorophyllin, orthosilicic acid, *lactobacillus acidophilus*, or combinations thereof.

The composition of the invention may be used as a supplement (e.g. health and/or nutritional supplement). Such a supplement may be, for example, as a food supplement to animals (e.g., mammals). The composition of the invention may be given to a wide variety of animals, including livestock such as camels, cattle, sheep, and the like, as well as pets such as dogs and cats. Further, as mentioned above, the invention is particularly useful for providing supplements to horses.

In certain embodiments, the supplement of the invention may further contain one or more additional nutrients, such as, vitamins, minerals, amino acids, proteins, herbs, oils, or combinations thereof. These nutrients are intended to provide additional nutritive support for the animals, particularly, horses. In certain embodiments, the additional nutrient included in a supplement of the invention is a vitamin.

Specific supplements routinely added to a horse's diet include, but are not limited to, Vitamins A, the B-complexes, C, D, E; chemical entities such as MSM, DMG, etc.; minerals including copper, manganese, selenium, cobalt, iron, phosphorus, zinc, sulfur, etc.; proteins such as Glucosamine HCl, Glucosamine Sulfate, Chondroitin Sulfate, Perna Mussel; Electrolytes such as sodium, potassium, chloride, magnesium, etc.; naturally derived substances, such as Brewer's Yeast, Bee Pollen, and Yucca; and herbs including Devil's claw, Echinacea, mint, St. John's wort, etc.

In addition, there are other additives that may be routinely added to a horse's feed. These include, but are not limited to: 1) daily dewormer, used to control intestinal parasites, 2) feed through insecticide, which is believed to prevent flies from using horse manure as a breeding ground, and 3) garlic, which is believed to repel flies. For purposes of this disclosure, the term supplements or nutrients will be used to describe all additives that are customarily added to feed prior to consumption.

Although the present description of the invention is generally directed to use of the invention with horses, it should be understood that the invention can be used in the same manner with other animals, including pets and livestock.

The invention also provides a feed supplement formulation to livestock, which comprises a composition described above. Particularly, the feed supplement formulation may comprises about 5 to 20 weight percentage of a sea buckthorn fruit powder, and about 5 to 20 weight percentage of glutamine.

In a specific embodiment, a composition or formulation of the invention includes about 7.5% w/w of L-glutamine, about 6.25% w/w of sea buckthorn fruit powder, about 6.25% w/w of lecithin, about 0.625% w/w of aloe vera extract, and about 0.625% w/w of pectin.

The composition or formulation of the invention may be in a form acceptable in the industry. For example, the formulation may be in a liquid, pellet, pill, gel, capsule, tablet, film, powder, crystal, or paste form. In one embodiment, a composition or formulation of the invention is in a pellet form.

Another aspect of the invention provides an animal feed containing a composition or composition or formulation described herein.

The composition or formulation of the invention may include compounds containing one or more asymmetric centers, which thus occur as racemates and racemic mixtures, single enantiomers, individual diastereomers and diastereomeric mixtures. All such isomeric forms of the compounds are expressly included in the present invention. These compounds may also be represented in multiple tautomeric forms, in such instances, the invention expressly includes all tautomeric forms of the compounds. All such isomeric forms of such compounds are expressly included in the present invention.

Further, the invention provides the use of a composition described herein, alone or together with one or more additional active agents and inactive agents in the manufacture of a food supplement, either as a single composition or as separate composition forms, for alleviation, treatment or prevention in a subject of a condition, disease, disorder or symptom set forth herein.

As discussed above, certain aspects of the invention provide a feed or an animal food supplement. Thus, the feed or the food supplement of the invention may be designed to be palatable to animals for which it is intended, e.g., by using flavors, aromas and textures that appeal to the animal to be fed. The selection of flavors, aromas, and textures appropriate for a given subject, i.e., the design of a palatable product, is well within the skill of the ordinary artisan and is, therefore, not discussed further here.

Methods

In one aspect, the invention provides a method of alleviating, treating, or preventing an ulcer-associated condition in a subject identified in need thereof. In certain embodiments, the method involves administering a composition of the invention to the subject simultaneously with or without food (e.g., a feed).

The subject is a mammal, such as, a human or nonhuman animal (e.g., rabbit, rodent, or primate). The subject contemplated herein may be animals of livestock, including, for example, bovine, equine, camel, cattle, sheep, and the like, as well as pets such as dogs and cats. As mentioned above, the invention is particularly useful for alleviating, treating, or preventing an ulcer-associated condition in horses.

The condition that can be treated, prevented, or alleviated is a symptom or condition associated an ulcer including, such as, a gastric ulcer, stomach ulcer (or peptic ulcer), venous ulcer, ulcerative sarcoidosis, ulcerative lichen planus, ulcerative colitis, mouth ulcer, corneal ulcer, dermatological ulcers, and etc. For example, the symptom or condition herein is associated with a gastric ulcer or stomach ulcer in the subject.

In one particular preferred aspect, supplementation feed with a supplement composition of the invention to a subject, e.g. a horse, can aid in protecting a nonglandular stomach of the animal (e.g. horse) from rebound acid effects after an omeprazole treatment is discontinued in the animal (e.g. horse).

One embodiment of the invention provides that the method of the invention is used for alleviating, treating, or preventing Equine Gastric Ulcer Syndrome (EGUS) in horses.

In certain embodiments, the subject could have been identified as having one or more of the diseases or disorders described herein. Identification of the diseases or disorders as described herein by a skilled physician or veterinarian is routine in the art and may also be suspected by the individual.

The composition of the invention can be administered to the subject through an oral administration. Other possible routes of administration include, for example, without limitation sublingual, transmucosal, intravenous, subcutaneous, intranasal, topical, etc.

According to another embodiment of the invention, the composition of the invention may be combined with other therapeutic agents. These therapeutic agents may be those known effective in alleviating, treating or preventing in the subject a same or different ulcer-related disease or condition. It is so contemplated that such combinations may, in some cases, provide better results or synergistic effects.

It is intended that the additional therapeutic agent(s) may be administered to the subject prior to, concurrently with, or subsequent to the administration of the composition of the invention.

The therapeutic agents can be, for example, small molecule therapeutics, natural products, and/or extracts that have been known and/or used in the industry for the treatment of ulcer-associated condition or symptoms in a subject. In certain cases, the therapeutic agents may be, such as, H2 blockers, proton-pump inhibitors, antibiotics, antacids, acid blockers, anti-inflammatory drugs, buffers, protectants, probiotics, etc.

For example, the therapeutic agent may be omeprazole (sold under tradename GASTROGARD®PRILOSEC® and etc.), or a pharmaceutically effective salt, solvate, hydrate, diastereomer, produg, or metabolite thereof. Omeprazole, a proton pump inhibitor used in the industry in the treatment of conditions, such as, dyspepsia, peptic ulcer disease (PUD), gastroesophageal reflux disease (GORD/GERD), laryngopharyngeal reflux (LPR) and Zollinger-Ellison syndrome, has the chemical structure as follows:

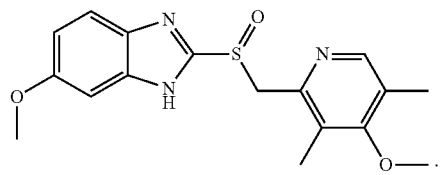 [SMILES: COc1ccc2nc(S(=O)Cc3ncc(C)c(OC)c3C)[nH]c2c1]

As another example, the therapeutic agent may be esomeprazole magnesium (tradename NEXIUM®), lansoprazole (tradename PREVACID®), pantoprazole (tradename SOMAC®, TECTA®, PANTOLOC®, etc.), and like, or a pharmaceutically effective salt, solvate, hydrate, diastereomer, produg, or metabolite thereof.

It is so contemplated that the composition of the invention and the other therapeutic agent(s) may be administered to the subject through the same route or by different routes.

In accordance with the invention, the composition can be administered to the subject once or multiple times a day. In certain embodiments, the composition is administered once, twice, three or four times a day.

As discussed above, the invention includes methods to alleviate, treat or prevent an ulcer-associated condition in a subject without significantly altering a gastric juice pH value of the subject.

In a preferred aspect of the invention, a composition of the invention alleviates, treats, or prevents the ulcer-associated condition in a subject without significantly altering a gastric juice pH value of the subject.

As above discussed, the subject that can be treated by a method of the invention may have been identified as susceptible to one or more of the diseases, disorders or conditions as described herein. The susceptibility of a subject may be based on any one or more of a number of risk factors and/or diagnostic approaches appreciated by the skilled artisan, including, but not limited to, genetic profiling, medical history, development history, appearance or signs of related conditions, endoscopic examination, types of feed, lifestyle (e.g., amount of exercise), or onset of certain disorders or symptoms within a herding population.

The terms "effective amount", "pharmaceutically effective amount", and "therapeutically effective amount" as used herein refer to an amount of a composition sufficient to alleviate, treat or prevent a specified condition (e.g., disease, disorder, etc.) or one or more of its symptoms and/or to prevent the occurrence of the condition. In reference to ulcer-associated conditions, an effective amount comprises an amount sufficient to, among other things, prevent, reduce, or eliminate the growth or severity of the ulcers.

In addition, the method of the invention may be used in conjunction with other prevention or treatment methods, such as, surgery, diet control and/or adjustment, change of lifestyle (e.g., amount of exercise, turnout), etc.

The optimal combination of one or more of surgery and/or additional agents in conjunction with administration of the compositions thereof described herein can be determined by an attending physician or veterinarians on the subject and taking into consideration the various factors affecting the particular subject including those described herein.

A separate aspect of the invention provides a method of preparing a food supplement formulation and/or medicament that is useful for the purposes and objects above delineated.

Kits and Dosages

The invention also provides a kit, which contains a composition or formulation as described above. The kit may come with written instructions for administration of the composition or formulation to a subject including, such as, a wide variety of animals. In certain aspects, the subject is an animal including a mammal (such as, humans, primates, livestock and pets), especially, a horse.

The written instructions may also include instructions for mixing the composition to be mixed with an animal feed. Furthermore, the written instructions may generally include information for use of the composition in alleviating, treating, or preventing an ulcer-associated condition in a subject.

In other embodiments, the instructions include at least one of the following: description of the components of the composition; dosage schedule and administration for alleviation, treatment or prevention of a condition or symptom delineated thereof; precautions; warnings; indications; counter-indications; over dosage information; adverse reactions; animal pharmacology; clinical studies; and/or references. The instructions may be printed directly on the container (when present), or as a label applied to the container, or as a separate sheet, pamphlet, card, or folder supplied in or with the container.

The following non-limiting examples are illustrative of the invention.

EXAMPLE 1

Supplement Composition and Administer

A preferred health supplement (referred to herein as Supplement composition) has the following components in admixture:

Form: Pellets

| Ingredients (80 g): | |
|---|---|
| L-Glutamine | 6,000 mg |
| Sea Buckthorn | 5,000 mg |
| Lecithin | 5,000 mg |
| Calcium Carbonate | 5,000 mg |
| Hydrolyzed Collagen | 3,000 mg |
| Magnesium Carbonate | 3,000 mg |
| Deglycyrrized Licorice | 2,000 mg |
| Magnesium Silicate | 2,000 mg |
| Fructooligosaccharides (FOS) | 1,500 mg |
| Mannanoligosaccharides (MOS) | 1,500 mg |
| Glycine | 1,000 mg |
| Gamma Oryzanol | 600 mg |
| Aloe Vera | 500 mg |
| Pectin | 500 mg |
| Slippery Elm | 350 mg |
| Marshmallow Root Extract | 300 mg |
| Sodium Copper Chlorophyllin | 112 mg |
| Orthosilicic Acid (Silica) | 100 mg |
| Lactobacillus Acidophilus | 750 million CFU |
| Fillers* | to balance of weight |

*Fillers of the above composition contained the following materials in admixture: Alfalfa Meal, Dried Grains with Solubles, Dried Oryzae Fermentation Extract Dried Subtillis Fermentation Extract, Fenugreek Grape Pomace (Ground Grape Seed) Lignin Sulfonate, Maltodextrin, Propionic Acid, Vegetable Oil (cold pressed).

The above Supplement composition may be administered as follows. For use in horses, administer 80 g daily per horse; 1 scoop of Supplement composition pellets=40 g (2 scoops daily).

EXAMPLE 2

Equine Health Studies

Eight healthy Thoroughbred and Thoroughbred-cross horses from the Equine Health Studies Program (EHSP) herd were used in this study. The study was performed as a 42-day 2-period crossover using a treatment group (n=8) and an untreated control (n=8).

All horses were stall-confined and fed mixed grass hay and sweet feed (OMOLENE® 100; Gray Summit, Mo.). Horses were assigned to the two treatment groups stratified by gastric ulcer score recorded on day 1 of period 1. Treated horses were fed with a Supplement composition of Example 1 above (40 g, twice daily) added to the sweet feed and control horses received no feed supplement.

Prior to beginning the study, all horses underwent physical examination. From Day 1 to Day 14, all horses were treated with omeprazole (GASTROGARD® paste, Merial Limited, Duluth, Ga.; 4 mg/kg, orally q24 h), then omeprazole was discontinued for the remainder of the study. All the horses remained stall-confined. From Day 28 to Day 35, all the horses underwent feed-deprivation, where they were muzzled and deprived of feed for 24 hours and then fed for 24 hours for a total of 96 hours to induce ulcers.

During the feed-deprivation days, the horses were fed 10% of their normal sweet feed, and the treated horses received the Supplement composition of Example 1 above (SMARTPAK® Equine, Plymouth, Mass.). From Day 35 to Day 42, all the horses returned to their normal diet to allow for recovery. The timelines of the events occurring during the period of the 42-day study were depicted in FIG. 1.

Gastroscopic examinations were performed on all the horses on Day 0, 14, 28, 35 and 42 and nonglandular gastric ulcer number (NGN) and severity (NGS) scores were assigned by the PI (FMA) who was masked to treatment (FIG. 2) (MacAllister et al. 1997). During gastroscopy, gastric juice was aspirated and pH measured.

FIG. 3 (a-d) are gastroscopic images of the nonglandular mucosa in a horse treated with a Supplement composition of Example 1 above. Gastric ulcers were observed on Day 1, then healed by Day 14, after the omeprazole and treatment with the Supplement composition of Example 1. Ulcer remained healed on Day 28, 14 days after omeprazole was discontinued. On Day 35, after the feed-deprivation, small focal ulcers were seen (circle).

FIG. 4 (a-d) gastroscopic images of the nonglandular mucosa in an untreated control horse. Gastric ulcers were observed on Day 1, then healed by Day 14, after the omeprazole treatment. Ulcers recurred on Day 28, 14 days after omeprazole was discontinued. On Day 35, after the feed-deprivation, the ulcers were still present (circles).

Figure 5:
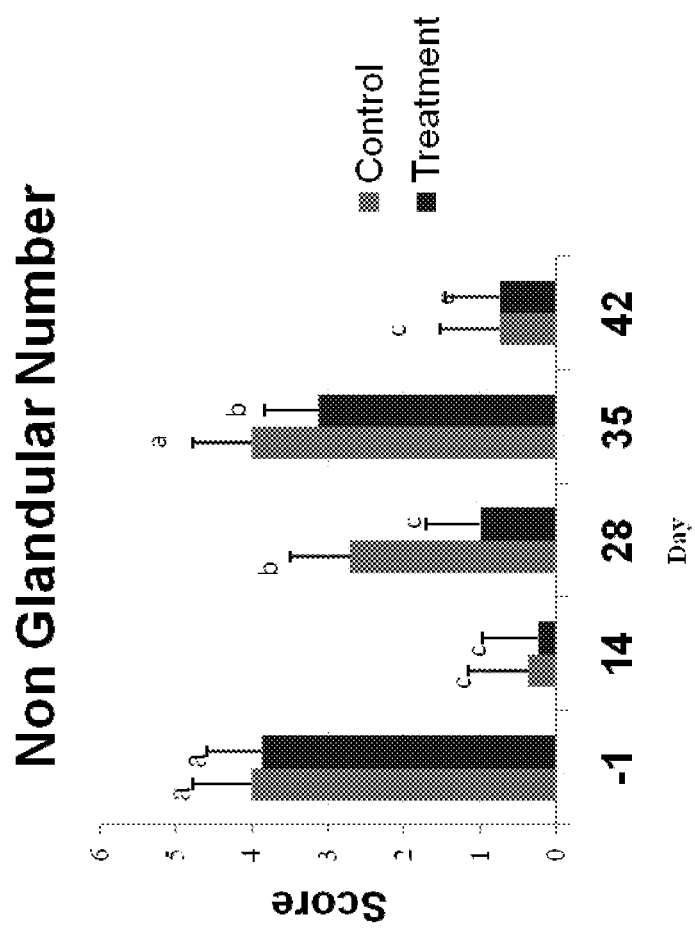
FIG. 5 is a graph presenting mean non-glandular number scores in 1) horses treated with a Supplement composition of Example 1 (Treatment) and 2) control horses (Control).
Figure 6:
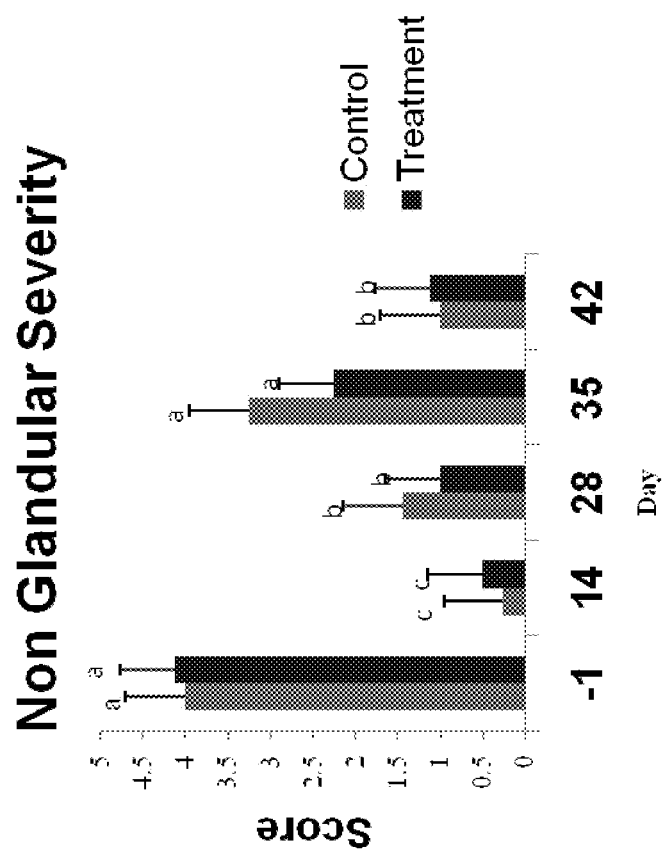
FIG. 6 is a graph showing non-glandular ulcer severity in in 1) horses treated with a Supplement composition of Example 1 (Treatment) and 2) control horses (Control).

On Day 1 before the omeprazole or Supplement composition of Example 1-treatment, NGN and NGS scores were not statistically different (P>0.05) in the group treated with the Supplement composition of Example 1 compared to the untreated controls (FIG. 5 & FIG. 6).

By Day 14, NGN and NGS scores significantly decreased (P<0.05) in both groups. The NGN score remained significantly lower in the horses treated with the Supplement composition of Example 1 above when compared to the untreated controls on Days 28 and 35. By Day 42, NGN and NGS scores were not significantly different in either group.

Figure 7:
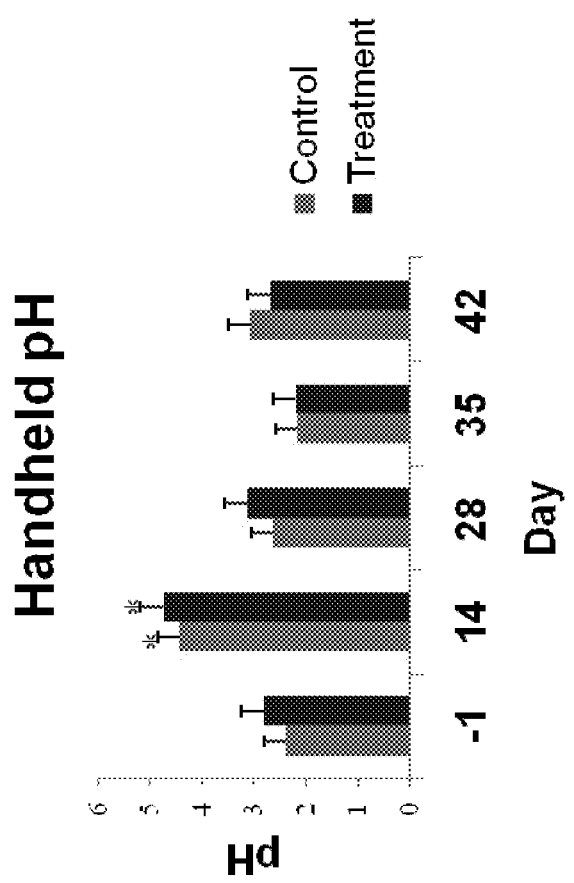
FIG. 7 is a graph depicting mean gastric juice pH value in in 1) horses treated with a Supplement composition of Example 1 (Treatment) and 2) control horses (Control).

Gastric juice pH values were significantly higher on Day 14 in both groups, when compared to other days. There was not a treatment effect on the gastric juice pH at any day during the study (FIG. 7).

General Health and Daily Observation were within normal limits in all the horses during the study periods. It was found that the Omeprazole treatment significantly decreased NGN and NGS scores, healing gastric ulcers in 6/8 (75%) horses in each of the study groups by Day 14.

The administered Supplement composition of Example 1 (40 gm, mixed with feed twice daily) was readily consumed by all horses in the study. No adverse effects due to treatment with the Supplement composition of Example 1 above were observed in the treated horses.

Two weeks after the omeprazole treatment (Day 28), the number of gastric ulcers increased significantly in the untreated control group, which was likely due to a rebound in an acid secretion. By contrast, treatment with the Supplement composition of Example 1 above resulted in lower NGN scores by Day 28 after the omeprazole treatment was discontinued, when compared to the untreated controls. It is believed that the Supplement composition of Example 1 above prevented the increase in the number of gastric ulcers 2 weeks after the omeprazole treatment and blunted the increase in the number of gastric ulcers after the feed-deprivation as well.

The horses treated with Supplement composition of Example 1 above had significantly lower NGN scores by Day 35 after feed-deprivation when compared to untreated controls. It was found that the gastric juice pH increased significantly by Day 14, due to the omeprazole treatment.

Gastric juice pH values can be determined as follows: gastric juice of a subject animal is aspirated through the biopsy channel of an endoscope and pH is measured at specified time intervals, particularly 1 hour before and then 1 hour after administration of a therapeutic agent or Supplement composition as disclosed herein. Gastric juice pH values can be compared between the times.

Further, it was found that treatment with the Supplement composition of Example 1 above did not increase the gastric juice pH in any of the horses in this study. There was no significant difference in the group treated with the Supplement composition of Example 1 above by the end of the study period. It was thus concluded that the Supplement composition of Example 1 above (40 g, twice daily) added to the feed prevented the worsening of gastric ulcers in stall-confined horses after the omeprazole treatment, without altering the gastric juice pH values in the horses.

Such administration of a supplement composition of the invention to a horse can aid in protecting a nonglandular stomach of the horse from rebound acid effects after an omeprazole treatment is discontinued in the horse.

EXAMPLE 3

This study was a blinded, two period cross-over with eight adult female horses. Each treatment phase consisted of a control group, that received feed only, and a treatment group that received a commercially available product containing sea buckthorn berries (SBC; SEABUCK™ Complete) (90 ml or 3 oz) twice daily mixed with grain feed. The treatment phase (60 days) was immediately followed by a prevention phase that consisted of a seven day alternating feed-deprivation model to induce or worsen existing ulcers. Gastroscopy was performed, using standard procedures, on each horse before each treatment period (Day 0), again on Day 30, Day 60, and following the alternating feed-deprivation period (Day 67).

At each endoscopic examination gastric juice was aspirated from the stomach and pH was measured along with overall non-glandular (NG) EGUS gastric ulcer score, NG ulcer severity, and NG ulcer number. Between each treatment period the horses had a four week washout period. All horses received the two treatments. The data was analyzed as a cross over ANOVA model in SAS (PROC MIXED Statistical Analysis Software) was used with significant differences considered, P<0.05

Figure 10:
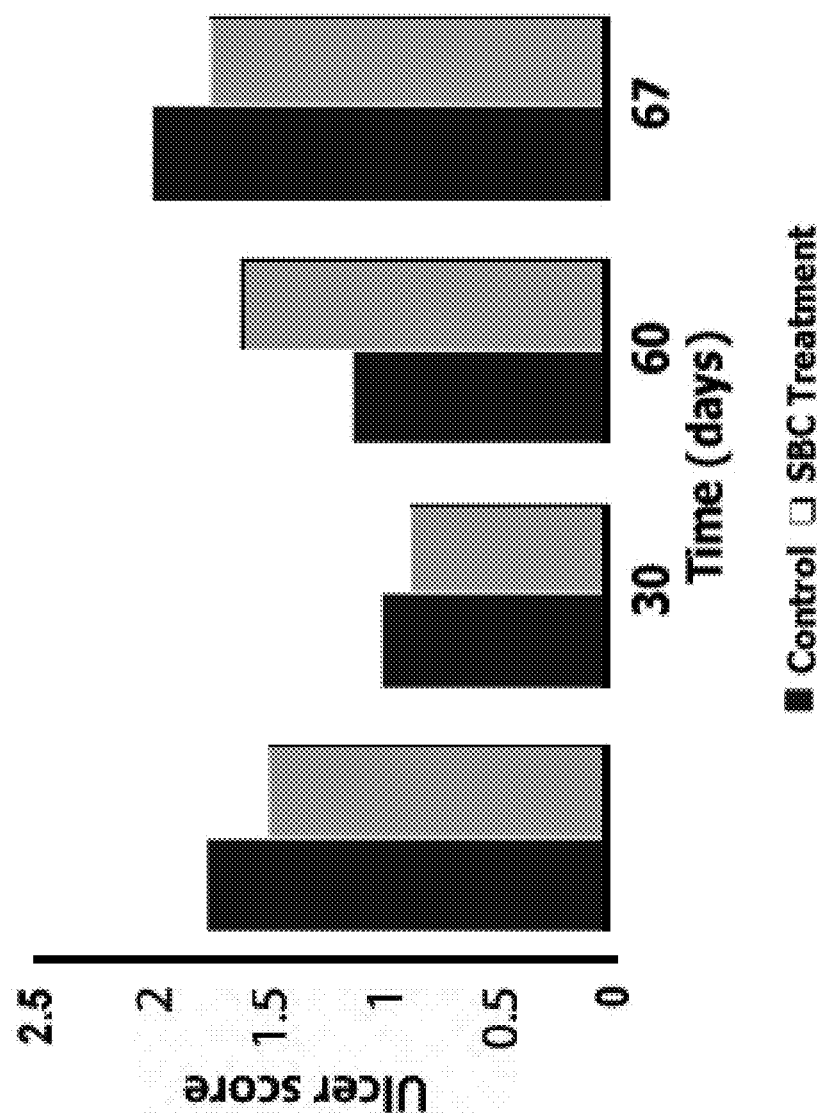
FIG. 10 is a graph depicting non-glandular gastric ulcer scores in untreated control horses and those treated by a composition containing sea buckthorn berries (SBC) after an alternating feed deprivation model.

It was observed that SBC was readily consumed by all horses in the study and no adverse affects were seen. However, gastric ulcer scores remained the same in SBC-treated horses after alternating the feed deprivation phase (Day 60-67), whereas ulcer scores increased in the untreated control during the same period (FIG. 8). The change in ulcer score was not significantly different (FIG. 10).

Figure 11:
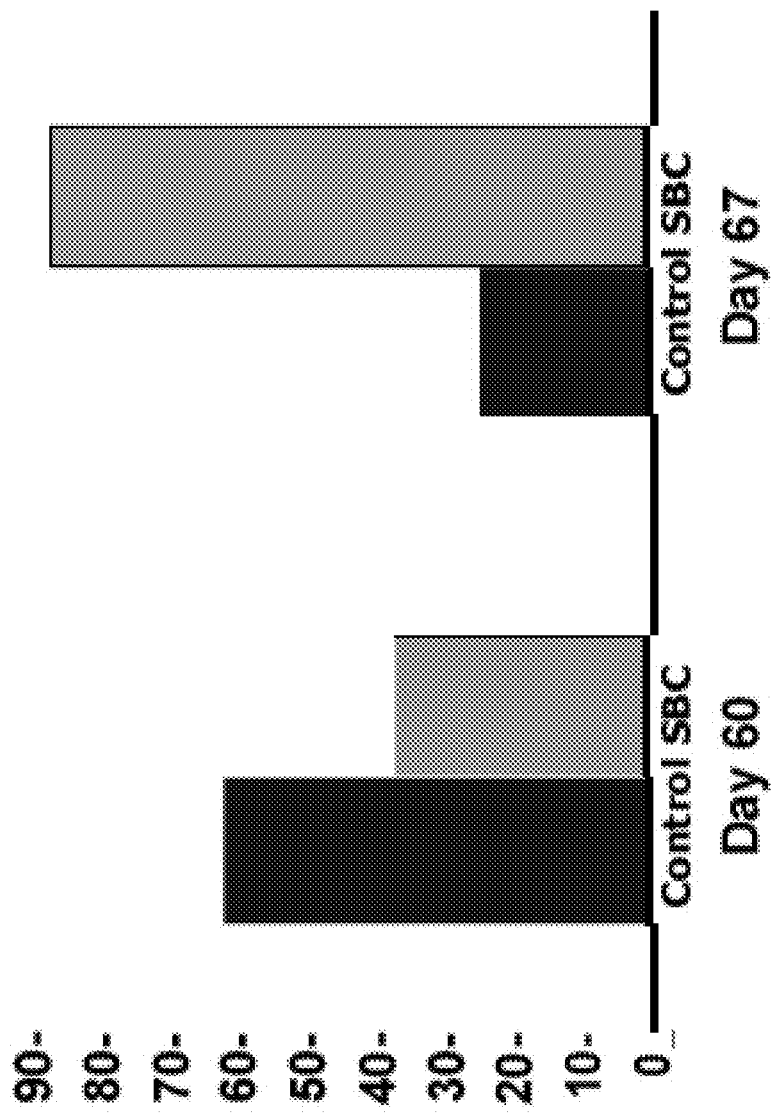
FIG. 11 is a graph showing that percentage of non-glandular gastric ulcer scores that were improved or stayed the same in untreated control horses (n=8) and those treated by a composition containing sea buckthorn berries (SBC) after an alternating feed deprivation model.

Further, gastric juice pH did not significantly change in the SBC-treated horses when compared to control horses (FIG. 9). It was noted that, during the feed deprivation phase, NG ulcer scores improved or stayed the same in 7/8 (88%) SBC-treated horses, compared to 2/8 (25%) of the control horses (FIG. 11).

Although the commercially available product (i.e., SBC) did not significantly decrease gastric ulcer scores during the treatment phase, it was concluded that active ingredients contained in sea buckthorn berries have some efficacy in preventing the worsening of ulcers during stress.

INCORPORATION BY REFERENCE

The entire contents of all patents, published patent applications and other references cited herein are hereby expressly incorporated herein in their entireties by reference.

Those skilled in the art will recognize, or be able to ascertain using no more than routine experimentation, numerous equivalents to the specific procedures described herein. Such equivalents are considered to be within the scope of this invention and are covered by the following claims.

REFERENCES

The following documents are cited herein.

MacAllister, C. G, Andrews F. M., Deegen, E., Ruoff W., and Olovson, S-G. *A scoring system for gastric ulcers in the horse*, Equine Vet. J. 6: 430-433, 1997.

Huff, N. K. et. al, *Effect of Seabuckthorn Berries and Pulp in a Liquid Emulsion on Gastric Ulcer Scores and Gastric Juice pH in Horses*, Journal of Veterinary Internal Medicine, 2012.

Reese R. E. et. al. *The effect of Seabuckthorn extract on the prevention and treatment of gastric ulcers in horses.*

Andrews, F. M., *Equine Gastric Ulcer Syndrome, American Association of Equine Practitioners*, July 2012 (2003).

Videla Ricardo, Andrews F. M., *New Perspectives in Equine Gastric Ulcer Syndrome*, 291-296 (2009).

Geetha S. et al., *Anti-oxidant and immunomodulatory properties of seabuckthorn (Hippophae rhamnoides) an in vitro study*, J. of Ethnopharmacology, 2002; 79:373-378.

Beveridge T. et al., *Seabuckthorn Products: Manufacturing and composition*, J. Agric. Food Chem., 1999; 47:3480-3488.

Xing J. et al., *Effects of sea buckthorn (Hippophae rhamnoides L.) see and pulp oils on experimental models of gastric ulcer in rats*, Fitoterapia, 2002; 73:644-650.

We claim:

1. A method of treating an ulcer in a horse in need thereof, consisting essentially of:

administering to said horse a therapeutically effective amount of a composition consisting essentially of sea buckthorn, glutamine, aloe vera extract, pectin and lecithin.

\* \* \* \* \*